(12) United States Patent  
Kawakami et al.

(10) Patent No.: US 9,089,457 B2
(45) Date of Patent: Jul. 28, 2015

(54) BODILY FLUID ABSORBENT ARTICLE

(75) Inventors: Yusuke Kawakami, Kagawa (JP); Atsushi Tsukuda, Kagawa (JP); Hitomi Nakao, Kagawa (JP)

(73) Assignee: Unicharm Corporation, Ehime (JP)

( * ) Notice: Subject to any disclaimer, the term of this patent is extended or adjusted under 35 U.S.C. 154(b) by 138 days.

(21) Appl. No.: 13/819,728

(22) PCT Filed: Sep. 16, 2011

(86) PCT No.: PCT/JP2011/005267
§ 371 (c)(1),
(2), (4) Date: Feb. 28, 2013

(87) PCT Pub. No.: WO2012/035787
PCT Pub. Date: Mar. 22, 2012

(65) Prior Publication Data
US 2013/0165882 A1    Jun. 27, 2013

(30) Foreign Application Priority Data

Sep. 16, 2010  (JP) .................. 2010-208654
Feb. 16, 2011  (JP) .................. 2011-031405

(51) Int. Cl.
*A61F 13/15* (2006.01)
*A61F 13/537* (2006.01)
(Continued)

(52) U.S. Cl.
CPC ....... *A61F 13/53717* (2013.01); *A61F 13/4756* (2013.01); *A61F 13/47218* (2013.01);
(Continued)

(58) Field of Classification Search
CPC ........... A61F 13/49001; A61F 13/4756; A61F 13/4704; A61F 13/47218; A61F 13/533; A61F 13/534; A61F 13/535; A61F 13/536; A61F 13/538; A61F 2013/4587; A61F 2013/53016; A61F 2013/530175; A61F 2013/5315; A61F 2013/53445; A61F 2013/53472; A61F 2013/5349; A61F 2013/5355; A61F 2013/5383
USPC .................. 604/368, 374, 375, 380
See application file for complete search history.

(56) References Cited

U.S. PATENT DOCUMENTS

| 4,327,729 A | 5/1982 | King |
| 4,842,594 A | 6/1989 | Ness |

(Continued)

FOREIGN PATENT DOCUMENTS

| JP | 54-449853 | 4/1979 |
| JP | 60-59105 | 4/1985 |

(Continued)

OTHER PUBLICATIONS

European Search Report from corresponding European Application No. 11824800.4 dated Mar. 4, 2014 (11 pgs).

(Continued)

*Primary Examiner* — Lynne Anderson
(74) *Attorney, Agent, or Firm* — Brinks Gilson & Lione

(57) ABSTRACT

A bodily fluid absorbent article adapted to absorb bodily fluid over a wide range thereof. An absorbent structure in the bodily fluid absorbent article includes an upper absorbent component and a lower absorbent component. The absorbent structure further includes one of a dispersing surface constituting the upper absorbent component and kept in contact with the lower absorbent component and a dispersing surface constituting the lower absorbent component and kept in contact with the upper absorbent component. Such dispersing surface exhibits a dispersion velocity for bodily fluid higher than those exhibited by the absorbent sections defined immediately above and under this dispersing surface.

5 Claims, 10 Drawing Sheets

(51) Int. Cl.
*A61F 13/538* (2006.01)
*A61F 13/475* (2006.01)
*A61F 13/472* (2006.01)
*A61F 13/535* (2006.01)
*A61F 13/45* (2006.01)
*A61F 13/534* (2006.01)
*A61F 13/53* (2006.01)

(52) U.S. Cl.
CPC ............ *A61F13/535* (2013.01); *A61F 13/538* (2013.01); *A61F 13/534* (2013.01); *A61F 2013/15406* (2013.01); *A61F 2013/15439* (2013.01); *A61F 2013/4587* (2013.01); *A61F 2013/5307* (2013.01); *A61F 2013/53445* (2013.01); *A61F 2013/53734* (2013.01); *A61F 2013/53739* (2013.01); *A61F 2013/53778* (2013.01)

(56) References Cited

U.S. PATENT DOCUMENTS

| | | | |
|---|---|---|---|
| 5,462,537 A * | 10/1995 | Carr et al. | 604/368 |
| 5,746,729 A * | 5/1998 | Wada et al. | 604/378 |
| 5,785,696 A | 7/1998 | Inoue et al. | |
| 5,846,231 A * | 12/1998 | Fujioka et al. | 604/380 |
| 5,846,891 A | 12/1998 | Fujioka et al. | |
| 6,099,515 A * | 8/2000 | Sugito | 604/385.01 |
| 6,118,042 A | 9/2000 | Palumbo | |
| 6,437,214 B1 * | 8/2002 | Everett et al. | 604/378 |
| 6,465,711 B1 | 10/2002 | Brisebois | |
| 7,279,613 B2 * | 10/2007 | Nozaki et al. | 604/380 |
| 2002/0065498 A1 * | 5/2002 | Ohashi et al. | 604/379 |
| 2003/0119405 A1 * | 6/2003 | Abuto et al. | 442/361 |
| 2004/0061263 A1 | 4/2004 | Daniels et al. | |
| 2005/0090789 A1 | 4/2005 | Graef et al. | |

FOREIGN PATENT DOCUMENTS

| | | |
|---|---|---|
| JP | 08-196559 | 8/1996 |
| JP | 09-051913 | 2/1997 |
| JP | 9-510633 | 10/1997 |
| JP | 2002-238948 | 8/2002 |
| JP | 2003-116917 | 4/2003 |
| JP | 2008-006203 | 1/2008 |
| JP | 2008-136564 | 6/2008 |
| JP | 2008-154605 | 7/2008 |
| WO | WO 2004/060415 A1 | 7/2004 |

OTHER PUBLICATIONS

International Search Report based on corresponding PCT application No. PCT/JP2011/005267 dated Dec. 20, 2011 (4 pgs).

* cited by examiner

БОДILY FLUID ABSORBENT ARTICLE

RELATED APPLICATION

This application is a 35 U.S.C. §371 national phase filing of International Patent Application No. PCT/JP2011/005267, filed Sep. 16, 2011, through which and to which priority is claimed under 35 U.S.C. §119 to Japanese Patent Application Nos. 2010-208654, filed Sep. 16, 2010 and 2011-031405filed Feb. 16, 2011.

TECHNICAL FIELD

The present disclosure relates to bodily fluid absorbent articles adapted to be used as urine absorbent pads, sanitary napkins or the like.

BACKGROUND ART

Conventionally, a menstruation pad as one example of bodily fluid absorbent articles is well known and a menstruation pad including a centrally convex absorbent structure is also well known.

For example, the absorbent article disclosed in JP 2002-238948 A (PTL 1) is exemplarily described on the basis of a sanitary napkin wherein the absorbent structure includes an upper absorbent component and a lower absorbent component shaped to be smaller than the upper absorbent component and on which the upper absorbent component is layered. This sanitary napkin is provided on its side facing the wearer's skin with the centrally convex absorbent region.

The absorbent article disclosed in JP 2008-6203 A (PTL 2) is exemplarily described on the basis of a sanitary napkin wherein the absorbent structure includes a first centrally convex layer and a second centrally convex layer. The first centrally convex layer defines a region of the absorbent structure being thicker than its periphery and the second centrally convex layer defines the region layered on the first centrally convex layer and is thicker than the first centrally convex layer. This absorbent structure is formed by locally compressing a lower absorbent component and layering an upper absorbent component on the compressed region of the lower absorbent component. The lower absorbent component defines the first centrally convex layer and the lower absorbent component cooperates with the upper absorbent component layered thereon to define the second centrally convex region.

CITATION LIST

Patent Literature

{PTL 1} JP 2002-238948 A
{PTL 2} JP 2008-6203 A

SUMMARY OF INVENTION

Technical Problem

The bodily fluid absorbent article, such as the sanitary napkin, having the bodily fluid absorbent structure provided with the centrally convex region facilitates the centrally convex region to be kept in close contact with the wearer's bodily fluid excretory organ, assuring that the centrally convex region can collect bodily fluid in a concentrated manner. However, the centrally convex component is usually formed of a mass or an aggregation of liquid-absorbent fibers or mixture of the liquid-absorbent fibers and super-absorbent polymer particles and the bodily fluid having been once collected by the centrally convex component cannot smoothly disperse into the periphery of the centrally convex region. In consequence, it is impossible for the bodily fluid absorbent article to absorb bodily fluid completely and the wearer may often experience a significant feeling of wetness.

An object of the present invention is to improve the bodily fluid absorbent article of known art so that the wearer's bodily fluid can be absorbed over a wide range of the absorbent structure even when the absorbent structure includes the centrally convex region.

Solution to Problem

The present invention has first, second and third aspects. According to the first, second and third aspects of the present invention, respectively, there is provided a bodily fluid absorbent article having a longitudinal direction and a thickness direction and comprising a liquid-pervious topsheet, a liquid-pervious or liquid-impervious backsheet and an absorbent structure sandwiched between the top- and backsheets as viewed in the thickness direction. The absorbent structure includes amass or an aggregation of liquid-absorbent materials at least including liquid-absorbent fibers and wrapped with one or more wrapping sheets, and a dispersing surface facilitating bodily fluid to be dispersed, and wherein at least a portion of one of the wrapping sheets located above as viewed in the thickness direction is liquid-pervious.

The present invention according to the first aspect thereof further includes the absorbent structure including an upper absorbent component and a lower absorbent component both lying inside the one or more wrapping sheets and layered one on another in the thickness direction and the dispersing surface of the upper absorbent component which is kept in contact with the lower absorbent component or a dispersing surface of the lower absorbent component which is kept in contact with the upper absorbent component; and the liquid-absorbent fibers in the dispersing surface extending along the dispersing surface. Preferably, the orientation of the liquid-absorbent fibers in the longitudinal direction or the transverse direction, respectively, is higher in the dispersing surface than in a region of the respective absorbent component contacting the dispersing surface.

The second aspect thereof further includes the dispersing surface including a plurality of compressed regions formed by locally compressing the absorbent component in the thickness direction so as to be arranged intermittently in the longitudinal direction so that the compressed regions having respective areas gradually enlarging from a central region of the bodily fluid absorbent article toward opposite end regions in the longitudinal direction.

The third aspect thereof further includes the dispersing surface including a plurality of compressed regions formed by locally compressing the absorbent component in the thickness direction so as to be arranged intermittently in the longitudinal direction so that the compressed regions having respective densities gradually increasing from a central region of the bodily fluid absorbent article toward opposite end regions in the longitudinal direction.

Advantageous Effects of Invention

In the bodily fluid absorbent article according to the first aspect of the present invention, the absorbent structure includes one of the dispersing surface constituting the upper absorbent component and kept in contact with the lower absorbent component and the dispersing surface constituting the lower absorbent component and kept in contact with the upper absorbent component. The dispersion velocity of bodily fluid is higher in any one of the dispersing surface than in the region lying immediately above this dispersing surface and in the region lying immediately under this dispersing surface. When bodily fluid having been absorbed by the upper absorbent component moves down to the lower absorbent component and reaches this dispersing surface, bodily fluid disperses over this dispersing surface in the longitudinal direction and/or in the transverse direction of the bodily fluid absorbent article and simultaneously moves toward the lower absorbent component. In consequence, the absorbent structure can absorb and contain bodily fluid over a wide range including, for example, the opposite end regions in the longitudinal direction thereof.

The bodily fluid absorbent article according to the second aspect of the present invention includes the compressed regions arranged intermittently in the longitudinal direction of the bodily fluid absorbent article as the bodily fluid-dispersing means. The respective compressed regions having the areas gradually enlarging from the central region toward the end regions so that bodily fluid discharged onto the central region moves from the non-compressed region of relatively low density toward the respective compressed regions and then disperses toward the compressed regions formed in the end regions and each having a relatively large area. Consequently, bodily fluid can be absorbed over a wide range inclusive of the end regions of the absorbent structure.

One or more embodiments according to the third aspect of the present invention includes the compressed regions arranged intermittently in the longitudinal direction of the bodily fluid absorbent article. The compressed regions respectively have the densities gradually increasing from the central region toward the end regions. With such arrangement, bodily fluid discharged onto the central region moves from the non-compressed region having a relatively low density toward the compressed regions and this bodily fluid disperses toward the compressed regions formed in the end regions and having further higher density. In consequence, bodily fluid can be absorbed over a wide range inclusive of the end regions of the absorbent structure.

DESCRIPTION OF EMBODIMENTS

Details of a bodily fluid absorbent article according to the present invention will be more fully understood from the description of a urine absorbent pad, one or more embodiments of such an article are given hereunder with reference to the accompanying drawings.

Figure 1:
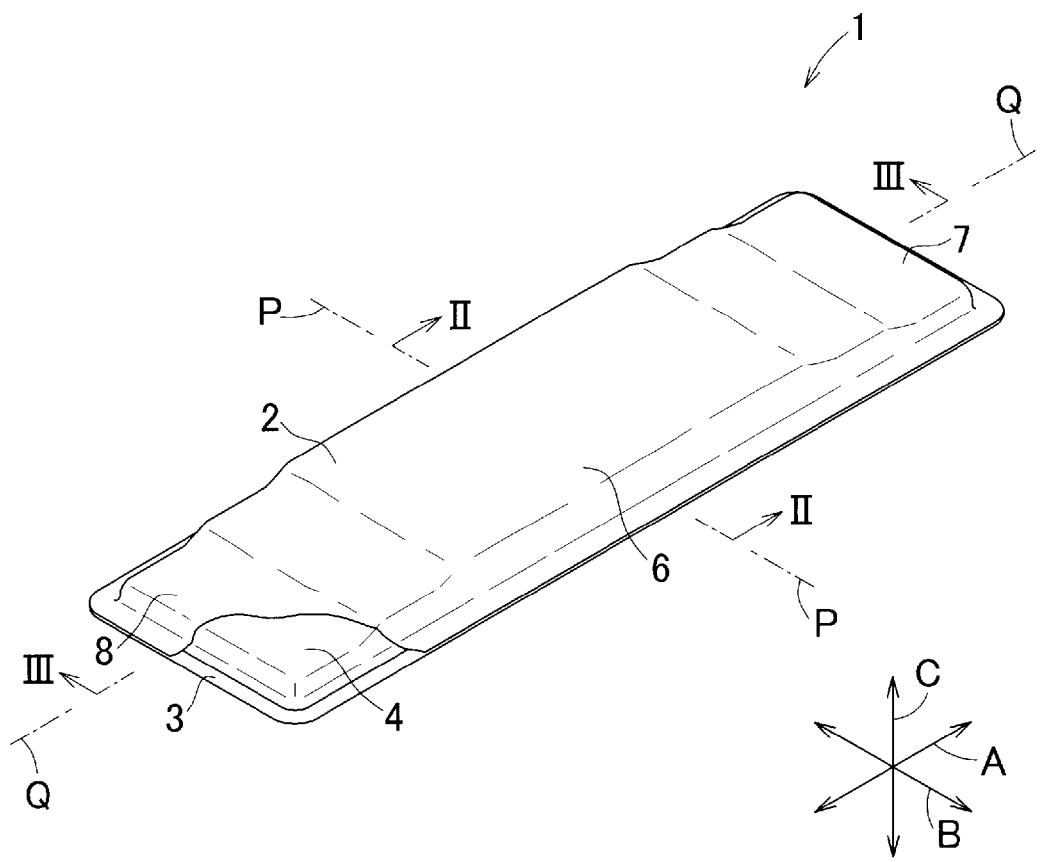
{FIG. 1}
A partially cutaway perspective view of a bodily fluid absorbent article (urine absorbent pad).

Referring to FIG. 1, a urine absorbent pad 1 has a longitudinal direction A, a transverse direction B and a thickness direction C and includes a liquid-pervious topsheet 2, a liquid-impervious backsheet 3 and a bodily fluid absorbent structure 4 sandwiched between the top- and backsheets 2, 3 in descending order as viewed in the longitudinal direction A. The backsheet 3 may alternatively be liquid pervious. Both the topsheet 2 and the backsheet 3 preferably extend outward beyond a peripheral edge of the absorbent structure 4, as shown, so as to overlap one another and these are preferably bonded together with hot melt adhesives (not shown), or otherwise, outside the peripheral edge. The pad 1 is preferably generally rectangular and the absorbent structure 4 is also preferably generally rectangular. The pad 1 is preferably formed symmetrically about a transverse center line P-P to bisect a length dimension of the pad 1 as well as about a longitudinal center line Q-Q to bisect a width dimension of the pad 1. The pad 1 is preferably relatively thick in a central region 6 defined in the vicinity of the transverse center line P-P and gradually thinned toward opposite end regions 7, 8 in the longitudinal direction A. In that sense, the pad 1 may be designated as a centrally convex pad. The pad 1 may be used together with a suitable undergarment such as a pant or pants, a diaper cover or a diaper.

Figure 2:
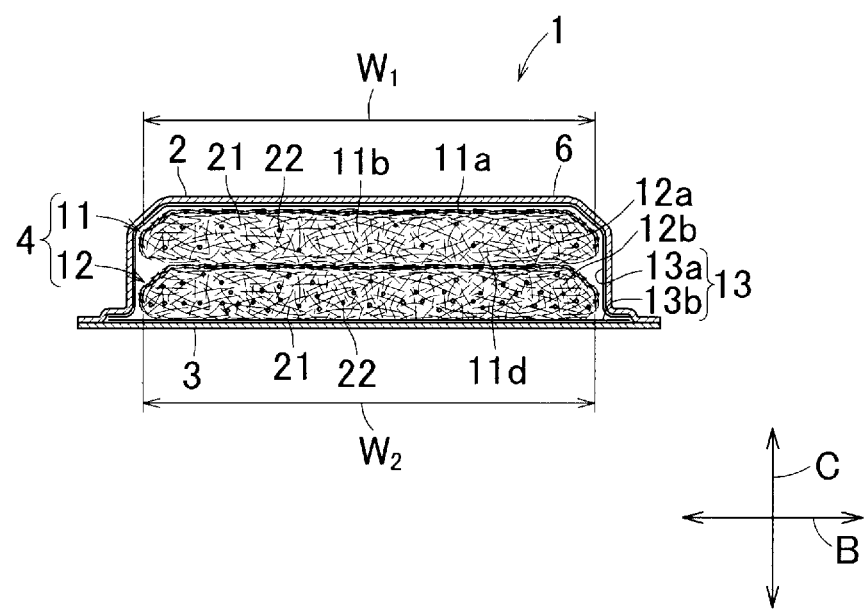
{FIG. 2}
A sectional view taken along line II-II in FIG. 1.

Referring to FIG. 2, the absorbent structure 4 includes a bodily fluid absorbent upper component 11 and a bodily fluid absorbent lower component 12 being layered one on another wherein these two absorbent components 11, 12 are wrapped with respective wrapping sheets 13. Whilst two wrapping sheets 13a, 13b are provided there may alternatively be a single wrapping sheet.

The upper absorbent component 11 is a mass or an aggregation of liquid-absorbent materials including liquid-absorbent fibers 21, such as, fluff wood pulp, semi-synthetic staple fibers such as rayon staple fibers, thermoplastic synthetic staple fibers, thermoplastic synthetic staple fibers having been treated to be hydrophilic, and preferably further includes super-absorbent polymer particles 22. As viewed in the thickness direction C of the pad 1, the upper absorbent component 11 preferably has an upper dispersing surface 11a and an upper absorbent layer 11b directly underlying the upper dispersing surface 11a. The upper dispersing surface 11a is a laminar portion defining a top surface of the upper absorbent component 11 and is preferably kept in close contact with a first wrapping sheet 13a of the wrapping sheets 13. In the upper dispersing surface 11a, the staple fibers and/or the fluff wood pulp as the liquid-absorbent fibers 21 accumulate with these fibers extending along the top surface. The upper absorbent layer 11b includes a bottom surface 11d of the upper absorbent component 11 and defines a major portion of the upper absorbent component 11 in the thickness direction thereof wherein the bottom surface 11d is kept in close contact with the lower absorbent component 12. In the upper absorbent layer lib, the aforementioned staple fibers and/or fluff wood pulp accumulate but such accumulation has no regularity. It is preferable that the upper dispersing surface 11a contains none of the super-absorbent polymer particles 22 and all or at least a majority of the super-absorbent polymer particles 22 in the upper absorbent component 11 are present in the upper absorbent layer 11b. Should the upper dispersing surface 11a contain the super-absorbent polymer particles 22, the super-absorbent polymer particles 22 may form a gel block upon absorption of bodily fluid and such gel block will interfere with the absorbing function expected for the absorbent structure 4.

The lower absorbent component 12 is amass or an aggregation of liquid-absorbent materials including materials similar to the liquid-absorbent fibers 21 described above. As viewed in the thickness direction C of the pad 1, the lower absorbent component 12 has a lower dispersing surface 12a and a lower absorbent layer 12b directly underlying the lower dispersing surface 12a. The lower dispersing surface 12a is a laminar portion defining a top surface of the lower absorbent component 12 and is kept in close contact with the bottom surface 11d of the upper absorbent component 11. In the lower dispersing surface 12a, staple fibers and/or fluff wood pulp forming the liquid-absorbent fibers 21 accumulate with the staple fibers and/or the fluff wood pulp extending along the top surface. The lower absorbent layer 12b defines a major portion of the lower absorbent component 12 in the thickness direction thereof and is preferably kept in close contact with a second wrapping sheet 13b of the wrapping sheets 13. In the lower absorbent layer 12b, the aforementioned staple fibers and/or fluff wood pulp accumulate on an irregular basis. It is preferable that the lower dispersing surface 12a does not contain the super-absorbent polymer particles 22 and all or at least a majority of the super-absorbent polymer particles 22 in the lower absorbent component 12 are present in the lower absorbent layer 12b. Should the lower dispersing surface 12a contain the super-absorbent polymer particles 22, the super-absorbent polymer particles 22 may form a gel block upon absorption of bodily fluid and such gel block may interfere with a smooth flow of bodily fluid from the upper absorbent component 11 toward the lower absorbent component 12.

The upper and lower absorbent components 11, 12 layered one on another are wrapped with the first (upper) and second (lower) wrapping sheets 13a, 13b. The first wrapping sheet 13a of the wrapping sheets 13 kept in close contact with the upper absorbent component 11 is liquid-pervious. The lower absorbent layer 12b of the lower absorbent component 12 is kept in close contact with the second wrapping sheet 13b. The second wrapping sheet 13b is preferably liquid-pervious or partially liquid-impervious. As the liquid-pervious first and second wrapping sheets 13a, 13b, for example, tissue paper, liquid-pervious nonwoven fabrics or liquid-pervious perforated plastic films may be used. As the liquid-impervious second wrapping sheet 13b, for example, liquid-impervious plastic films or liquid-impervious nonwoven fabrics may be used. When the second wrapping sheet 13b is liquid-impervious, a liquid-pervious sheet may preferably be used as the backsheet 3. Referring to FIG. 2, hot melt adhesives, or otherwise, may be used for bonding between the topsheet 2 and the first wrapping sheet 13a, between the first wrapping sheet 13a and the upper absorbent component 11, between the lower absorbent component 12 and the second wrapping sheet 13b, and between the second wrapping sheet 13b and the backsheet 3. It should be appreciated, however, that FIG. 2 exemplarily illustrates the case in which such adhesives are not used.

Figure 3:
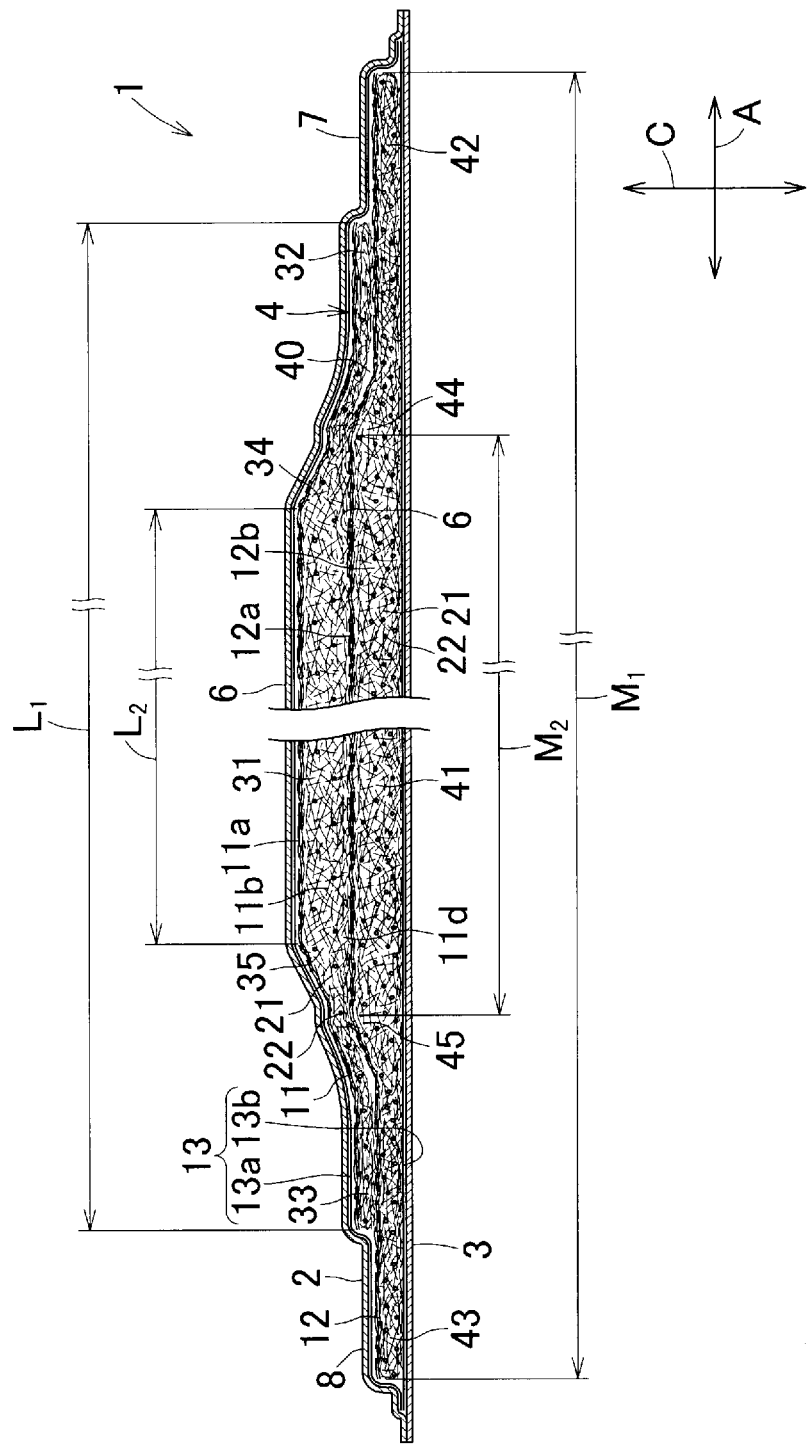
{FIG. 3} A sectional view taken along line III-III in FIG. 1.

FIG. 3 is a sectional view of the pad 1 taken along line III-III in FIG. 1 wherein the line III-III corresponds to the longitudinal center line Q-Q. Referring to FIG. 3, the upper absorbent component 11 preferably includes a first upper section 31 lying in the central region 6 of the pad 1 and having a substantially uniform thickness and second and third upper sections 32, 33 lying in opposite end regions 7, 8 of the pad 1 and having a relatively smaller thickness. The thickness of the pad 1 is preferably gradually reduced from the first upper section 31 toward the second upper section 32 and the third upper section 33 to define intermediate upper sections 34, 35. These first, second and third upper sections 31, 32, 33 and the intermediate upper sections 34, 35 are formed as a whole with the upper dispersing surface 11a and the upper absorbent layer 11b. The first upper section 31 is located in the central region of the upper absorbent component 11 as viewed in the longitudinal direction A and the second and third upper sections 32, 33 are located in the end sections of the upper absorbent component 11 opposed to each other in the longitudinal direction A about the first upper section 31.

The lower absorbent component 12 preferably includes a first lower section 41 lying in the central region 6 of the pad 1 and having a substantially uniform thickness and second and third lower sections 42, 43 lying in opposite end regions 7, 8 of the pad 1 and having a relatively smaller thickness. The thickness of the pad 1 is preferably gradually reduced from the first lower section 41 toward the second lower section 42 and the third lower section 43 to define intermediate lower sections 44, 45. These first, second and third lower sections 41, 42, 43 and the intermediate lower sections 44, 45 are formed as a whole with the lower dispersing surface 12a and the lower absorbent layer 12b. The first lower section 41 is located in the central region of the lower absorbent component 12 as viewed in the longitudinal direction A and the second and third lower sections 42, 43 are located in the end sections of the lower absorbent component 12 opposed to each other in the longitudinal direction A about the first lower section 41.

Referring to FIG. 3 with FIG. 2, the upper absorbent component 11 and the lower absorbent component 12 respectively have widths $W_1$, $W_2$ (See FIG. 2) as measured along the transverse center line P-P and lengths $L_1$, $M_1$ (See FIG. 3) as measured along the longitudinal center line Q-Q. The first upper section 31 of the upper absorbent component 11 and the first lower section 41 of the lower absorbent component 12 both lying in the central region 6 of the pad 1 respectively have lengths $L_2$, $M_2$ as measured along the longitudinal center line Q-Q. These dimensions may be appropriately selected depending on a wearer's age span and, in the case of the pad 1 for adult, for example, the width $W_1$ of the upper absorbent component 11 may be set to a range of 40 to 100 mm, the length $L_2$ may be set to a range of 200 to 300 mm and the length $L_2$ may be set to a range of 40 to 80% of the length $L_1$. While the width $W_2$ of the lower absorbent component 12 may be set to the same dimension as the width $W_1$ as in the present embodiment, it is possible to set the width $W_2$ to a dimension which is narrower than or equal to the width $W_1$. While the length $M_1$ of the lower absorbent component 12 may be the same as the length $L_1$ as in the present embodiment, it is also possible, for example, to set the length $M_1$ to be longer than the length $L_1$ by a range of 20 to 40 mm so that the thickness of the pad 1 may be gradually changed in the regions between the central region 6 and the end regions 7, 8 of the pad 1 with the upper absorbent component 11 layered on the lower absorbent component 12 as illustrated in FIG. 3.

In one embodiment of the pad 1, the first upper section 31 and the first lower section 41 respectively contain the liquid-absorbent fibers 21 in a range of 300 to 400 g/m² by mass and the second and third upper sections 32, 33 as well as the second and third lower sections 42, 43 respectively contain the liquid-absorbent fibers in a range of 100 to 250 g/m² by mass. When the upper absorbent component 11 and the lower absorbent component 12 respectively contain the super-absorbent polymer particles 22, content percentage of the super-absorbent polymer particles 22 in the respective absorbent components 11, 12 is preferably in a range of 35 to 75% by mass.

One example of the method to measure the content percentages of the super-absorbent polymer particles 22 in the upper absorbent component 11 and the lower absorbent component 12 includes the steps as follows: cutting away test pieces each having a size of 20×20 mm from the respective absorbent components 11, 12; weighing these test pieces; loosening these test pieces; separating the super-absorbent polymer particles 22 from the liquid-absorbent fibers 21 while these loosened test pieces are observed through a hand glass lens of 5 to 10 magnifications; weighing the liquid-absorbent fibers 21 and the super-absorbent polymer particles 22; and calculating content percentages of the super-absorbent polymer particles 22 in the upper absorbent component 11 and the lower absorbent component 12.

Another example of the method to measure the content percentages of the super-absorbent polymer particles 22 includes the steps as follows:

(1) The upper absorbent component 11 or the lower absorbent component 12 to be measured with respect to the content percentage of the super-absorbent polymer particles 22 contained therein is loosened to separate the super-absorbent polymer particles 22 from the liquid-absorbent fibers 21. Then about 1 g of the liquid-absorbent fibers 21 and about 1 g of the super-absorbent polymer particles 22 are sampled and weighed to obtain a dry mass of the liquid-absorbent fibers 21 and a dry mass of the super-absorbent polymer particles 22.

(2) The sampled liquid-absorbent fibers 21 and the super-absorbent polymer particles 22 are respectively put into separate 250-mesh nylon envelopes and immersed in 500 ml of physiologic saline for 30 minutes.

(3) The respective nylon envelopes are suspended in a standard testing condition in a testing laboratory room for 15 minutes to drain off water and then weighed to obtain a mass $R_P$ of the nylon envelope containing therein the liquid-absorbent fibers 21 and a mass $R_S$ of the nylon envelope containing therein the super-absorbent polymer particles 22. A water absorption rate $Q_P$ of the liquid-absorbent fibers 21 and a water absorption rate $Q_S$ of the super-absorbent polymer particles 22 are calculated from following equations:

Water absorption rate $Q_P$ (g/g) of the liquid-absorbent fiber={mass $R_P$−(mass of nylon envelope)−(dry mass of the liquid-absorbent fibers 21)}/(dry mass of the liquid-absorbent fibers 21).

Water absorption rate $Q_S$ (g/g) of the super-absorbent polymer particles 22={mass $R_S$−(mass of nylon envelope)−(dry mass of the super-absorbent polymer particles 22)}/(dry mass of the super-absorbent polymer particles 22).

(4) Now a 30 mm×30 mm test piece for measurement is cut away from the upper absorbent component 11 or the lower absorbent component 12 and weighed to obtain a dry mass $W_O$. A dry mass of the liquid-absorbent fibers 21 contained in this test piece is designated by $W_P$ and a dry mass of the super-absorbent polymer particles 22 contained in this test piece is designated by $W_S$.

(5) The test piece is put into 250 mesh nylon envelope and the nylon envelope is immersed in 500 ml of physiologic saline for 30 minutes and thereafter the nylon envelope is suspended in a standard testing condition in a testing laboratory room for 15 minutes to drain off water. This drained off envelope is weighed to obtain a wet mass $W_1$ of this wet test piece. From the dry mass $W_O$ and the wet mass $W_1$, an amount of water absorption $T_A$ (g) is determined and then dry masses $W_P$, $W_S$ of the liquid-absorbent fibers 21 and the super-absorbent polymer particles 22 are calculated from the following Math. 1:

$$W_C{}^* = W_P + W_S$$

$$T_A{}^* = W_1{}^* - W_O{}^*$$

$$T_A{}^* = Q_P{}^* \cdot W_P + Q_S{}^* \cdot W_S = Q_P{}^* W_P + Q_S{}^* (W_C{}^* - W_P) = (Q_P{}^* - Q_S{}^*) \cdot W_P + Q_S{}^* \cdot W_O{}^*$$

$$W_P = (T_A{}^* - Q_S{}^* \cdot W_C{}^*)/(Q_P{}^* - Q_S{}^*)$$

$$W_S = W_O{}^* - \{(T_A{}^* - Q_S{}^* \cdot W_O{}^*)/(Q_P{}^* - Q_S{}^*)\} \quad \{\text{Math. 1}\}$$

The above-mentioned procedure makes it possible to determine the content percentage (%) of the super-absorbent polymer particles 22 in the form of Math. 2.

$$(W_S/W_O{}^*) \cdot 100 \quad \{\text{Math. 2}\}$$

The "*" marked values in the abovementioned equations should be understood to be the values which can be directly obtained by measuring the test piece. The method of measuring the content percentage of the super-absorbent polymer particles 22 in this manner is preferably applied to the upper absorbent component and the lower absorbent component 12 in which the liquid-absorbent fibers 21 and the super-absorbent polymer particles 22 are integrated together so that these fiber 21 and particles 22 are not readily separated one from another.

Figure 4:
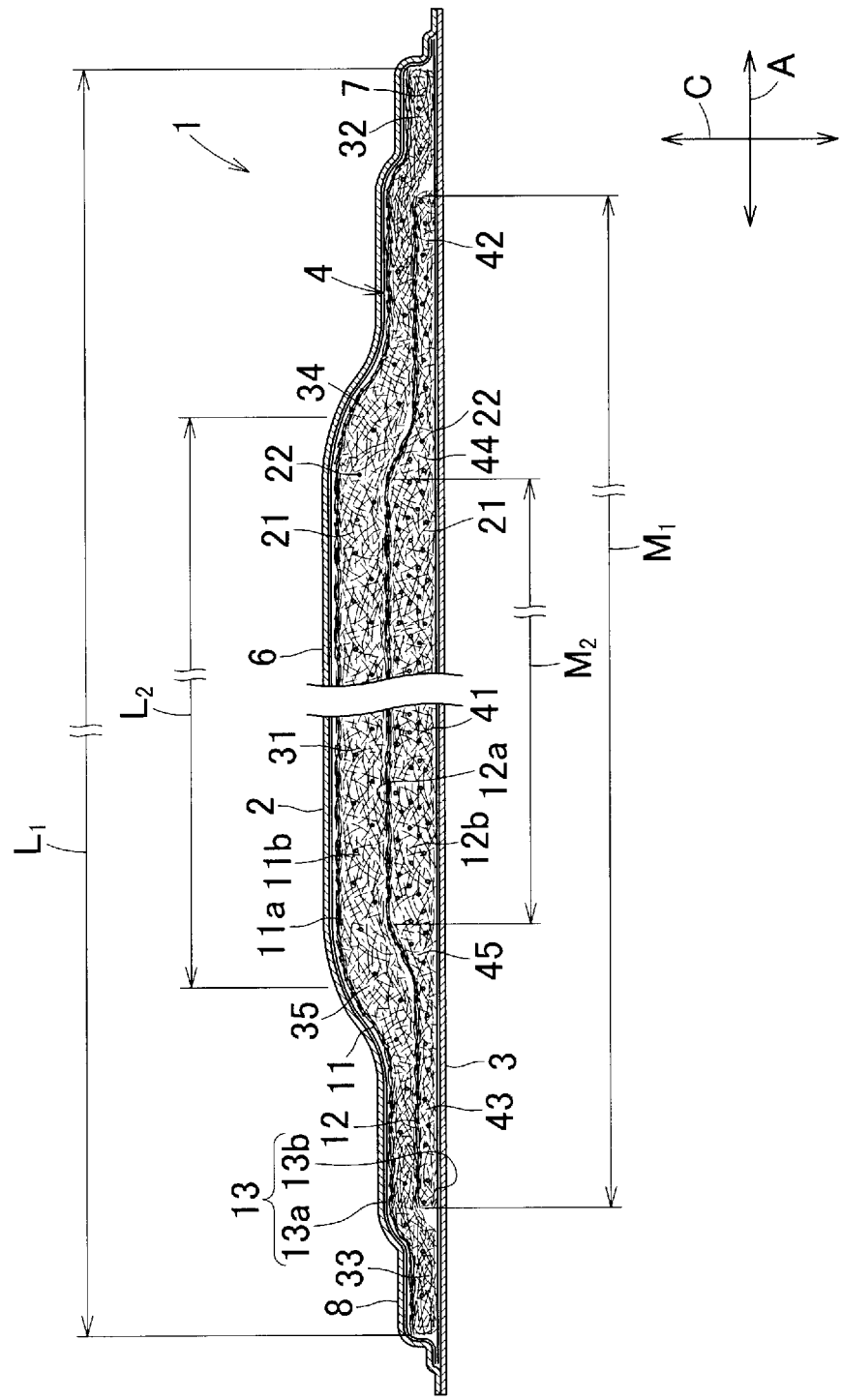
{FIG. 4}
A view similar to FIG. 3, showing one embodiment of the present invention.

Referring to FIG. 4, the pad 1 shown therein is distinguished from the pad 1 shown in FIGS. 2 and 3 in a dimensional relation between the upper absorbent component 11 and the lower absorbent component 12 in the longitudinal direction A of the pad 1. Specifically, the length $L_1$ of the upper absorbent component 11 is larger than the length $M_1$ of the lower absorbent component 12. The length $L_2$ of the first upper section 31 in the upper absorbent component 11 is larger than the length $M_2$ of the first lower section 41 in the lower absorbent component 12 and smaller than the length $M_1$ of the lower absorbent component 12. Also in the pad 1 shown in FIG. 4, the thickness of the pad 1 preferably undergoes a gradual change between the central region 6 and the end region 7 as well as between the central region 6 and the end region 8. Compared, for example, to the case in which the thickness of the lower absorbent component 12 sharply changes, an area over which the upper absorbent component 11 and the lower absorbent component 12 stack one on another can be increased and thereby the possibility that a gap might be left between these components 11, 12 can be restricted. In such pad 1, the end regions 7, 8 and the vicinities thereof can provide supple texture.

Figure 5:
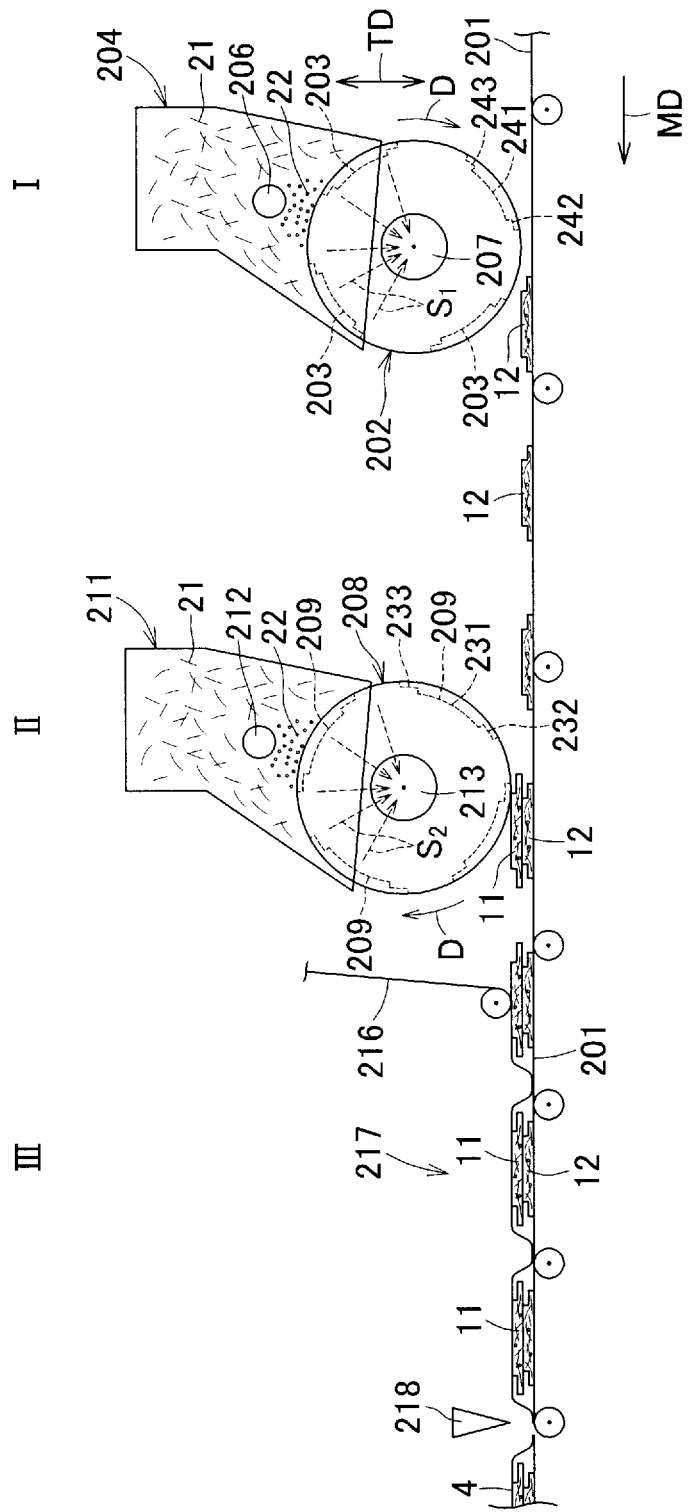
{FIG. 5}
A diagram exemplarily illustrating a process of making the bodily fluid absorbent article.

Referring to FIG. 5, a process of making the pad 1, specifically a process of forming the upper absorbent component 11 and the lower absorbent component 12 in FIG. 4 is illustrated.

In a step I of the process, a sheet-like first web 201 is continuously fed from the upstream side toward the downstream side in a machine direction MD. The first web 201 is material for the second wrapping sheet 13b in FIGS. 2 through 4 and runs below a first forming drum 202. The first forming drum 202 is formed on its peripheral surface with a plurality of shaping depressions 203 each having a shape corresponding to the shape of the lower absorbent component 12 in FIG. 4 and these depressions 203 are arranged intermittently in a circumferential direction of the first forming drum 202. Each of the depressions 203 includes a relatively deep first depression 241 adapted to form the first lower section 41 of the lower absorbent component 12 and relatively shallow second and third depressions 242, 243 adapted to form the second and third lower sections 42, 43. The first forming drum 202 rotates clockwise (i.e., in the direction D as indicated in FIG. 5) and the depression 203 is aligned with a feeding unit 204 provided above the first forming drum 202 as the depression 203 comes close to twelve o'clock position. While the feeding unit 204 feeds the liquid-absorbent fibers 21 (See FIG. 4) preferably containing at least fluff wood pulp downward into the depression 203, a polymer feeder 206 incorporated in the lower position of the feeding unit 204 in the vicinity of the first forming drum 202 feeds the super-absorbent polymer particles 22 (See FIG. 4) downward into the depression 203 so that the polymer particles may not be contained in the dispersing surface 12a. In the course of being supplied with the liquid-absorbent fibers 21 and the super-absorbent polymer particles 22, the depression 203 is in fluid-communication with a suction unit 207 and the liquid-absorbent fibers 21 are sucked together with the super-absorbent polymer particles 22 into the depression 203 so as to be accumulated therein. Then, the depression 203 having the fibers 21 and the polymer particles 22 accumulated therein leaves the feeding unit 204. Immediately after the depression 203 has been aligned with the feeding unit 204, the depression 203 is supplied primarily with a leading quantity of the liquid-absorbent fibers 21 so that the liquid-absorbent fibers 21 may extend just along the smooth surface of the depression 203 thereof under the suction effect $S_1$. In other words, this leading quantity of the liquid-absorbent fibers 21 accumulate on the surface of the depression 203 so that the fibers 21 may lie flat on the surface of the depression 203. A follow-on quantity of the liquid-absorbent fibers 21 is successively accumulated in the depression 203 but apt to be oriented at random in the longitudinal direction, in the transverse direction and in the depth direction of the depression 203. Outside the feeding unit 204, the liquid-absorbent fibers 21 and the super-absorbent polymer particles 22 accumulated together are separated from the depression 203 to form masses or aggregations substantially in the shape of the lower absorbent component 12 in FIG. 4 and placed on the first web 201. The masses or aggregations are arranged on the first web 201 intermittently in the machine direction MD and further run in this direction MD. It should be appreciated that, in the step I, it is possible to use any mechanical or pneumatic push-out means in order to separate the masses or aggregations of the liquid-absorbent fibers 21 and the super-absorbent polymer particles 22 accumulated together from the depression 203.

In a step II of the process illustrated in FIG. 5, the lower absorbent components 12 running in the machine direction MD together with the first web 201 pass below a second forming drum 208. The second forming drum 208 is formed on its peripheral surface with a plurality of shaping depressions 209 each having a shape corresponding to the shape of the upper absorbent component 11 in FIG. 4 and these depressions 209 are arranged intermittently in a circumferential direction of the second forming drum 208. Each of the depressions 209 includes a relatively deep first depression 231 adapted to form the first upper section 31 of the upper absorbent component 11 and relatively shallow second and third depressions 232, 233 adapted to form the second and third upper sections 32, 33. The second forming drum 208 rotates clockwise (i.e., in the direction D as indicated) and the depression 209 is aligned with a feeding unit 211 provided above the second forming drum 208 as the depression 209 comes close to twelve o'clock position. While the feeding unit 211 feeds the liquid-absorbent fibers 21 containing at least fluff wood pulp downward into the depression 209, a polymer feeder 212 incorporated in the lower position of the feeding unit 211 in the vicinity of the second forming drum 208 feeds the super-absorbent polymer particles 22 downward into the depression 209 so that the polymer particles 22 may not be contained in the dispersing surface 11a. In the course of being supplied with the liquid-absorbent fibers 21 and the super-absorbent polymer particles 22, the depression 209 is in fluid-communication with a suction unit 213 and the liquid-absorbent fibers 21 is sucked together with the super-absorbent polymer particles 22 into the depression 209 so as to be accumulated therein and leaves the feeding unit 211. Immediately after the depression 209 has been aligned with the feeding unit 211, the depression 209 is supplied primarily with the liquid-absorbent fibers 21 so that the liquid-absorbent fibers 21 may extend just along the smooth surface of the depression 209 in the longitudinal direction thereof under the suction effect $S_2$. In other words, the liquid-absorbent fibers 21 accumulate on the surface of the depression 209 so that the fibers 21 may lie down on the surface of the depression 209. The liquid-absorbent fibers 21 which subsequently accumulate are oriented at random in the longitudinal direction, in the transverse direction and in the depth direction of the depression 209. Outside the feeding unit 211, the accumulated liquid-absorbent fibers 21 and super-absorbent polymer particles 22 are separated from the depression 209 to form a mass in the shape of the upper absorbent components 11 in FIG. 4 and layered on the associated lower absorbent components 12 placed on the first web 201. These upper and lower absorbent components 11, 12 arranged on the first web 201 further run in the machine direction MD. In a similar fashion to the fibers 21 in the lower absorbent component 12 obtained in the step I, in the upper absorbent components 11 obtained in the step II, the liquid-absorbent fibers 21 accumulate so that the fibers 21 may lie flat on the surface of the depression 209.

The first web 201 on which the upper absorbent components 11 and the lower absorbent components 12 are placed runs to a step III. In the step III, a sheet-like second web 216 is continuously fed to the upper absorbent components 11 and the lower absorbent components 12 both placed on the first web 201 from above and cooperates with the first web 201 to sandwich the upper absorbent components 11 and the lower absorbent components 12 and thereby to form a composite web 217. The second web 216 is used to form the first wrapping sheet 13a in FIG. 4. The composite web 217 may be cut by a cutter 218 along lines defined each pair of the adjacent upper absorbent components 11, 11 to obtain the individual absorbent structure 4 shown in FIG. 4.

In the absorbent structure 4 obtained by the process illustrated in FIG. 5, the first, second and third upper sections 31, 32, 33 formed by intermediary of the intermediate sections 34, 35 in the upper absorbent component 11 have respective thickness conforming to shapes as well as depending on depths of the first, second and third depressions 231, 232, 233 in the depression 209. In a similar fashion, each of the first, second and third lower sections 41, 42, 43 formed by intermediary of the intermediate sections 44, 45 in the lower absorbent component 12 has a respective thickness conforming to shapes as well as depending on depths of the first, second and third depressions 241, 242, 243 in the depression 203. Thickness measurement for these sections 31, 32, 33, 41, 42, 43 and the absorbent structure was conducted using PEACOCK Digital Thickness Gauge manufactured by OZAKI MFG. CO. LTD. The measurement was carried out by placing a smooth metallic plate on the regions to be measured. It should be appreciated that the device used for this measurement is not limited to the above-mentioned gauge and any other device equivalent to the above-mentioned gauge may be used. As a measuring terminal of the gauge, a metallic disc having a diameter of 20 mm may be used and put in contact with an object to be measured at a contact pressure in a range of 5.0 to 5.5 g/cm$^2$. Thickness of the metallic disc may be subtracted from a measured result to obtain thickness of each section. In the lower absorbent component 12 obtained in the step I of FIG. 5, the liquid-absorbent fibers 21 accumulated directly on the surface of the depression 203 defines the lower dispersing surface 12a of the lower absorbent component 12 and the liquid-absorbent fibers 21 and the super-absorbent polymer particles 22 having been accumulated in the depression 203 after forming the lower dispersing surface 12a defines the lower absorbent layer 12b. In the upper absorbent component 11 obtained in the step II, the liquid-absorbent fibers 21 accumulated directly on the surface of the depression 209 defines the upper dispersing surface 11a of the upper absorbent component 11 and the liquid-absorbent fibers 21 and the super-absorbent polymer particles 22 having been accumulated in the depression 209 after formation of the upper dispersing surface 11a defines the upper absorbent layer 11b. The process illustrated in FIG. 5 may be modified so that the absorbent structure 4 is obtained in the step I and/or the step II without feeding the super-absorbent polymer particles 22 and this absorbent structure 4 is used to obtain the pad 1 according to the present invention. It is also possible in the first step I and/or the second step II to use fluff wood pulp, semi-synthetic staple fibers and the like independently or in the form of mixture thereof as the liquid-absorbent fibers 21.

With the pad 1 as exemplarily shown in FIGS. 1 through 4 comprising the upper absorbent component 11 and the lower absorbent component 12 obtained by the process as has been described above, bodily fluid discharged onto the central region 6 of the pad 1 penetrates the topsheet 2, then the first wrapping sheet 13a and is absorbed by the upper absorbent component 11. A portion of bodily fluid having been absorbed by the upper absorbent component 11 moves downward and is absorbed by the lower absorbent component 12. In the pad 1, the topsheet 2 is preferably adapted to let bodily fluid penetrate locally without allowing bodily fluid to disperse. While it is not essential for the first wrapping sheet 13a to disperse bodily fluid, it is preferable to use tissue paper well adapted for dispersion of bodily fluid as the first wrapping sheet 13a so that the first wrapping sheet 13a disperses bodily fluid having penetrated the topsheet 2 in the longitudinal direction A as well as in the transverse direction B of the pad 1. The bodily fluid having penetrated the first wrapping sheet 13a moves to the upper dispersing surface 11a defining the top surface of the upper absorbent component 11. In the upper dispersing surface 11a, the liquid-absorbent fibers 21 having been subjected to the suction effect in the process illustrated in FIG. 5 extend so as to lie on the top surface of the upper absorbent component 11 and therefore bodily fluid is dispersed over the upper dispersing surface 11a and simultaneously absorbed by the upper absorbent layer 11b. In the lower absorbent component 12 also, the liquid-absorbent fibers 21 having been subjected to the suction effect in the process illustrated in FIG. 5 extend so as to lie on the top surface of the lower absorbent component 12 and therefore bodily fluid moving from the upper absorbent component 11 to the lower absorbent component 12 is dispersed over the lower dispersing surface 12a and simultaneously absorbed by the lower absorbent layer 12b.

In the upper absorbent layer 11b and the lower absorbent layer 12b of the absorbent structure 4, the larger the distance from the respective dispersing surfaces 11a, 12a in the thickness direction C, the higher the irregularity at which the liquid-absorbent fibers 21 are accumulated and the lower the density of the respective layers 11b, 12b. Consequently, it may be difficult for bodily fluid to disperse in the respective layers 11b, 12b in the longitudinal direction A as well as in the transverse direction B. However, bodily fluid can easily disperse in the upper dispersing surface 11a and the lower dispersing surface 12a in the longitudinal direction A as well as in the transverse direction B and then move to the upper absorbent layer 11b and the lower absorbent layer 12b. In this way, bodily fluid absorption property of the upper absorbent layer 11b and the lower absorbent layer 12b is available over a wide range. In the pad 1, the upper dispersing surface 11a and the lower dispersing surface 12a function as means for dispersion of bodily fluid and thereby it is possible to prevent bodily fluid from staying in the central region 6. In consequence, the central region 6 should not force the wearer of the pad 1 to experience an uncomfortable feeling of wetness.

In the centrally convex pad 1 as illustrated, it would not necessarily be easy to utilize most part of the liquid-absorbent fibers 21 effectively for absorption of bodily fluid. However, the absorbent structure 4 according to the present embodiment includes the upper dispersing surface 11a and the lower dispersing surface 12a both adapted to disperse bodily fluid and thereby makes it possible to utilize most part of the liquid-absorbent fibers 21. This means that a large quantity of bodily fluid can be absorbed by the pad 1 and such pad 1 not only alleviates a feeling of wetness experienced by the wearer but also restricts leakage of bodily fluid.

In the pad 1, the upper absorbent component 11 is preferably in close contact with the lower absorbent component 12 but sometimes gaps 40 (See FIG. 3) may be left between these absorbent components 11, 12 and such gaps 40 would often prevent bodily fluid from smoothly moving from the upper absorbent component 11 to the lower absorbent component 12. However, as exemplarily shown in FIG. 3, the lower dispersing surface 12a extends across and beyond the respective gaps 40 in the longitudinal direction A so that bodily fluid discharged onto the central region 6 of the pad 1 may disperse over the lower dispersing surface 12a to the second upper section 32 of the upper absorbent component 11 as well as to the second lower section 42 of the lower absorbent component 12 both being at a large distance from the respective gaps 40 and be absorbed therein.

While the pad 1 comprising the upper absorbent component 11 and the lower absorbent component 12 preferably includes the upper dispersing surface 11a and the lower dispersing surface 12a, the lower dispersing surface 12a lying in a middle of the absorbent structure as viewed in the thickness direction C is particularly important for effective utilization of the lower absorbent layer 12b. The lower dispersing surface 12a is formed of the liquid-absorbent fibers 21 accumulated at a density higher than a density of the upper absorbent layer 11b lying immediately above the lower dispersing surface 12a as well as than a density of the lower absorbent layer 12b underlying the lower dispersing surface 12a. In addition, the lower dispersing surface 12a is formed of the liquid-absorbent fibers 21 accumulated on the surface of the depression 203 of the first forming drum 202 so as to extend in parallel to the surface thereof or on the surface of the depression 209 of the second forming drum 208 so as to extend along the surface thereof. In consequence, bodily fluid can disperse over the lower dispersing surface 12a at a high velocity in the longitudinal direction A and/or in the transverse direction B and quickly move to the lower absorbent layer 12b. Even the upper absorbent component 11 not having the upper dispersing surface 11a can be used as the component 11 of the pad 1 so far as the lower dispersing surface 12a exhibits the significant function as has been described above.

The dispersion velocity of bodily fluid in the upper absorbent component 11 and/or the lower absorbent component 12 can be visually determined by cutting the pad 1 using a sharp-edge tool and thereby making a test piece allowing a cross-section of the pad 1 in the thickness direction C to be observed. About 1 to 5 ml of test liquid such as artificial urine, artificial menstrual blood or physiologic saline may be fed drop by drop to the test piece from above the topsheet 2 so that progress of penetration of the test liquid into the pad 1 may be visually observed.

The present invention is not limited to the pad 1 including the absorbent structure 4 which includes, in turn, the upper absorbent component 11 and the lower absorbent component 12, as illustrated, but may be implemented in the form of the pad 1 using a panel-like additional absorbent component placed above the upper absorbent component 11 or in the form of the pad 1 using a panel-like additional absorbent component under the lower absorbent component 12. The upper absorbent component above which the additional absorbent component is placed preferably includes the upper dispersing surface 11a. When the additional absorbent component underlies the lower absorbent component 12, this additional absorbent component preferably includes a dispersing surface kept in contact with the lower absorbent component 12. While the exemplarily illustrated pad 1 is centrally convex in the central region 6 defined between the end regions 7, 8 as viewed in the longitudinal direction A, the pad 1 may be implemented also so that it is centrally convex in the central region defined between the lateral regions as viewed in the transverse direction B.

Furthermore, the present invention is not limited to the urine absorbent pad 1, and may be implemented also in the form of a bodily fluid absorbent wearing article such as a disposable diaper or a sanitary napkin or in the form of a bodily fluid absorbent member adapted to be attached to a disposable diaper, a diaper cover or the like.

Figure 6:
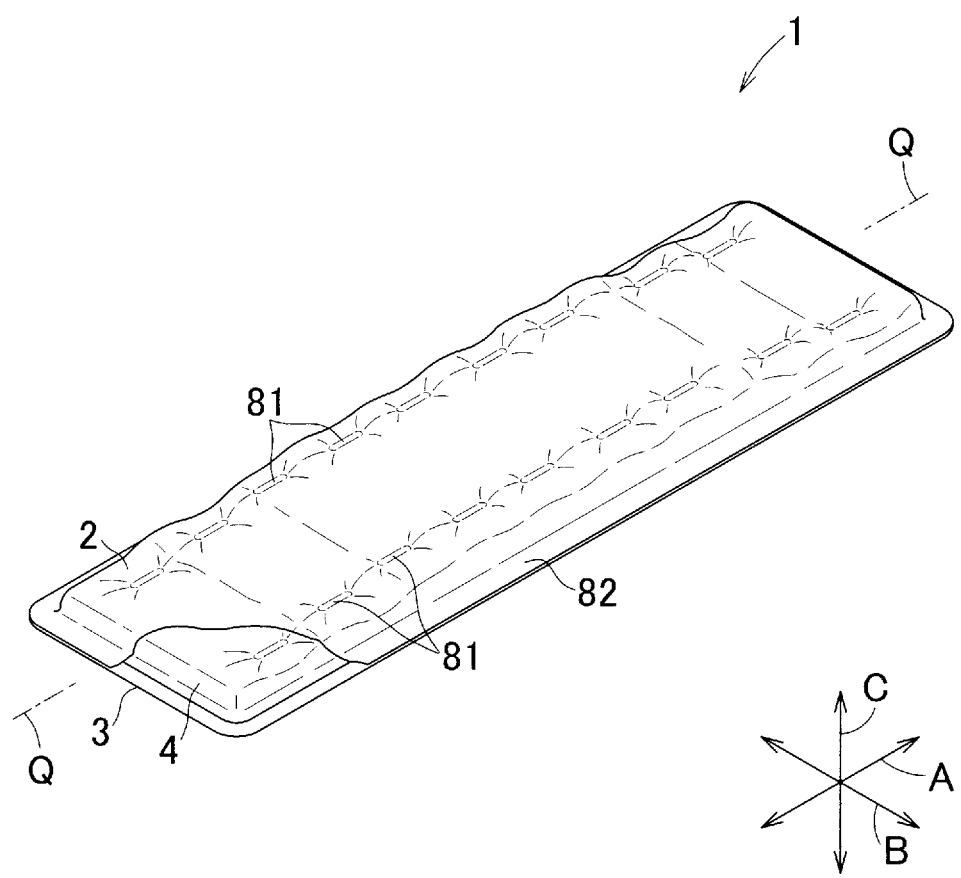
{FIG. 6}
A view similar to FIG. 1, showing another embodiment of the present invention.

FIG. 6 is a view similar to FIG. 1, showing another embodiment of the present invention. Referring to FIG. 6, the pad 1 exemplarily illustrated therein is formed along opposite side edges as viewed in the transverse direction B with compressed regions 81. These compressed regions 81 may be formed by locally compressing the side edges of the pad 1 of FIG. 1 in the direction from the topsheet 2 toward the backsheet 3. A mold used for such compression may be used at a room temperature or in a heated state and a temperature at which the mold is heated is preferably selected so that the thermoplastic synthetic resin ingredient is softened but not fused. In the compressed regions 81, the accumulation of the liquid-absorbent fibers 21 can be densified in comparison to the remaining region. The compressed regions 81 may be shaped in grooves extending continuously or, as exemplarily illustrated, intermittently in the longitudinal direction A along the side edges of the pad 1 to assure that bodily fluid can be dispersed in the longitudinal direction A of the pad 1 before bodily fluid flowing on the topsheet 2 in the transverse direction B of the pad 1 reaches opposite side edges 82 of the pad 1. In this way, it is possible to prevent bodily fluid from leaking beyond these side edges 82 of the pad 1. The upper absorbent component 11 and the lower absorbent component 12 overlapping the compressed regions 81 may be put in close contact with the compressed regions 81 to prevent these two absorbent components 11, 12 from being displaced from each other.

Figure 7:
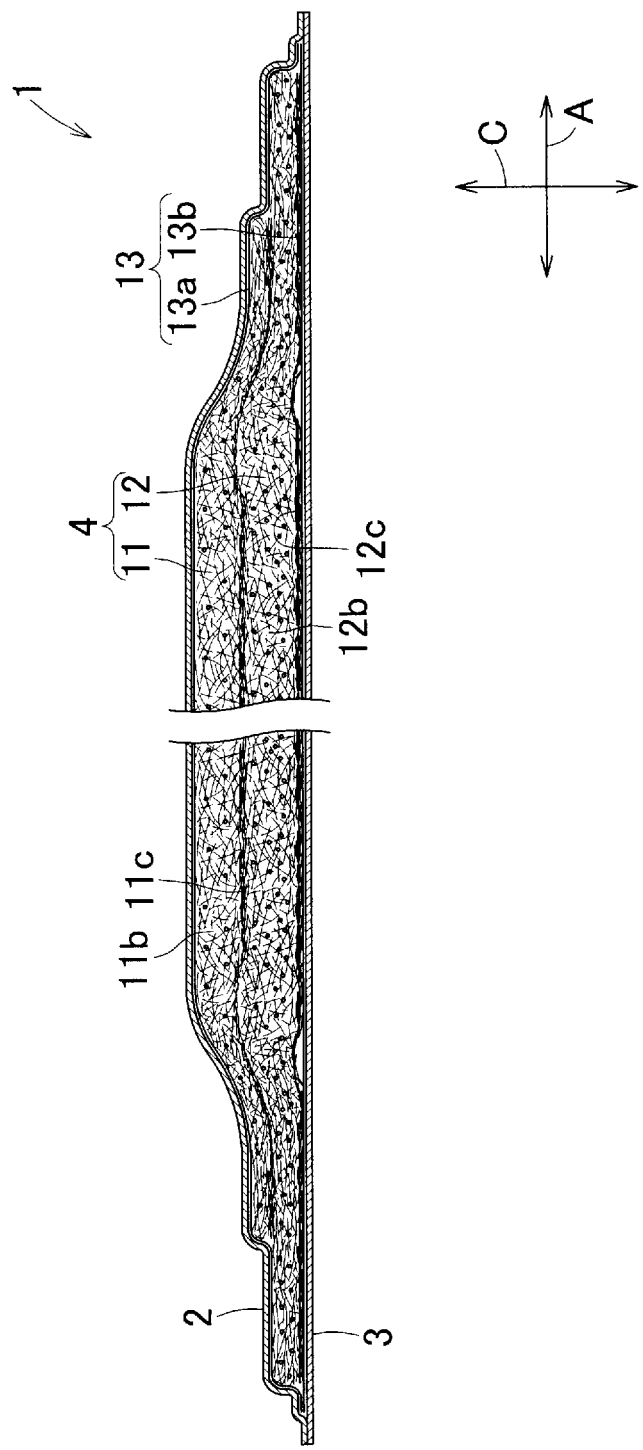
{FIG. 7}
A view similar to FIG. 3, showing still another embodiment of the present invention.

Referring to FIG. 7, while the pad 1 shown therein also includes the absorbent structure 4 comprising the upper absorbent component 11 and the lower absorbent component 12, the upper absorbent component 11 does not have the upper dispersing surface 11a kept in contact with the first wrapping sheet 13a as shown in FIG. 3 but rather an upper dispersing surface 11c is kept in contact with the lower absorbent component 12. The lower surface 12a of the lower absorbent component 12 is not kept in contact with the upper absorbent layer 11b of the upper absorbent component 11 but rather a lower dispersing surface 12c is kept in contact with the second wrapping sheet 13b.

The absorbent structure 4 of FIG. 7 can be obtained by making several alterations to the process of FIG. 5. In the absorbent structure 4 of FIG. 7, the first web 201 in FIG. 5 is used as stock material for the first wrapping sheet 13b and the second web 216 is used as stock material for the second wrapping sheet 13b. Of the respective absorbent components in FIG. 5, the lower absorbent component 12 in FIG. 5 is used as the upper absorbent component 11 in FIG. 7 and the upper absorbent component 11 in FIG. 5 is used as the lower absorbent component 12 in FIG. 7. Furthermore, the length of the depression 203 in the circumferential direction of the first forming drum 202 in FIG. 5 is changed to the length of the depression 209 in the circumferential direction of the second forming drum 208 in FIG. 5 and the length of the depression 209 in the circumferential direction of the second forming drum 208 in FIG. 5 is changed to the length of the depression 203 in the circumferential direction of the first forming drum 202 in FIG. 5. In the pad 1 of FIG. 7, the bodily fluid disperses over the upper dispersing surface 11c in the longitudinal direction A and/or in the transverse direction B at the higher velocity than in the upper absorbent layer 11b lying immediately above the upper dispersing surface 11c and the lower absorbent layer 12b immediately underlying the upper dispersing surface 11c. In consequence, bodily fluid moving down in the thickness direction C rapidly disperses over the upper dispersing surface 11c in the longitudinal direction A and/or in the transverse direction B and simultaneously moves into the lower absorbent layer 12b of the lower absorbent component 12 over a wide range.

Figure 8:
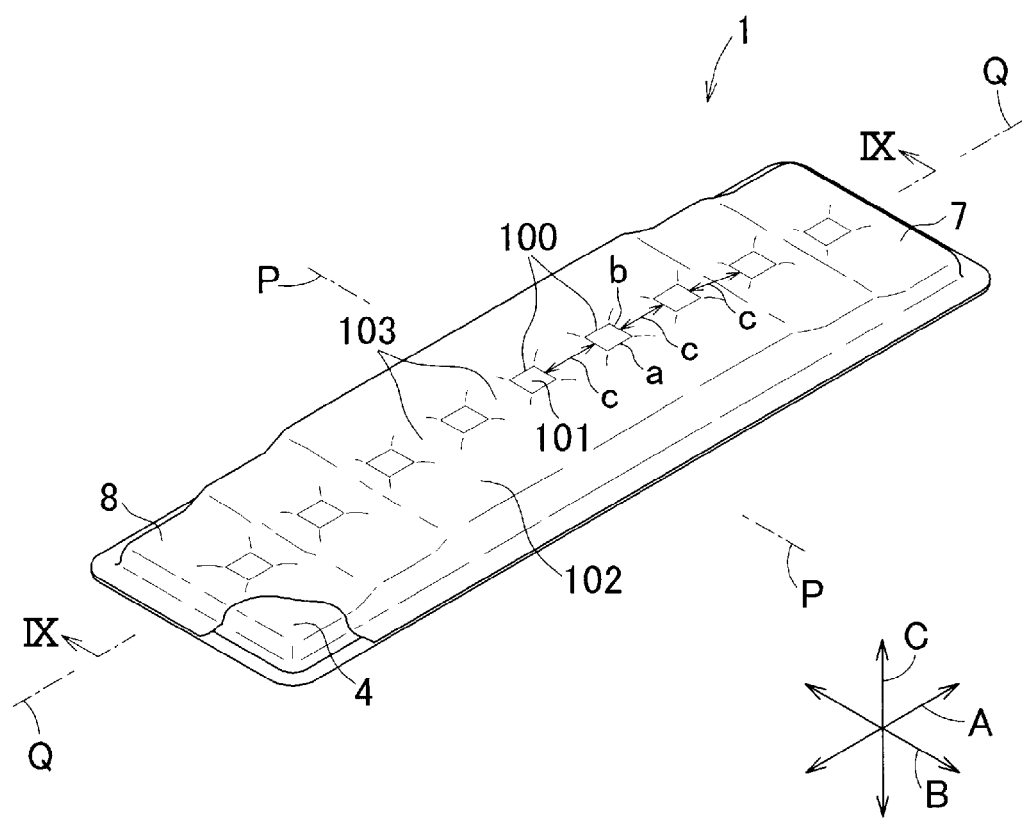
{FIG. 8}
A view similar to FIG. 1, showing yet another embodiment of the present invention.

Referring to FIG. 8, the pad 1 shown therein is distinguished from the pad 1 of FIG. 1 in that the pad 1 is formed in the middle as viewed in the transverse direction B of the pad 1 with a plurality of compressed regions 100 arranged intermittently in the longitudinal direction A. These compressed regions 100 may be formed by the same method as has been used to form the compressed regions 81 in FIG. 6, i.e., by locally compressing the pad 1 of FIG. 1 in the direction from the topsheet 2 toward the backsheet 3 (See FIGS. 1 and 2). In FIG. 8, each of the compressed regions 100 has a rectangular or square bottom surface 101 contoured by a dimensions a and b in the longitudinal direction A and in the transverse direction B, respectively, and each pair of the compressed regions 100, 100 being adjacent in the longitudinal direction A are spaced from each other by a dimension c. While these dimensions a, b, c may be set to appropriate values depending on a size of the pad 1 or the other factors, the case in which the dimension a is equal to the dimension b, i.e., the individual compressed region is square, and the dimension c is constant is exemplarily illustrated. The compressed regions 100 are surrounded by a non-compressed region 102 and this non-compressed region 102 includes intermediate regions 103 extending between each pair of the adjacent compressed regions 100 and having a dimension c.

Figure 9:
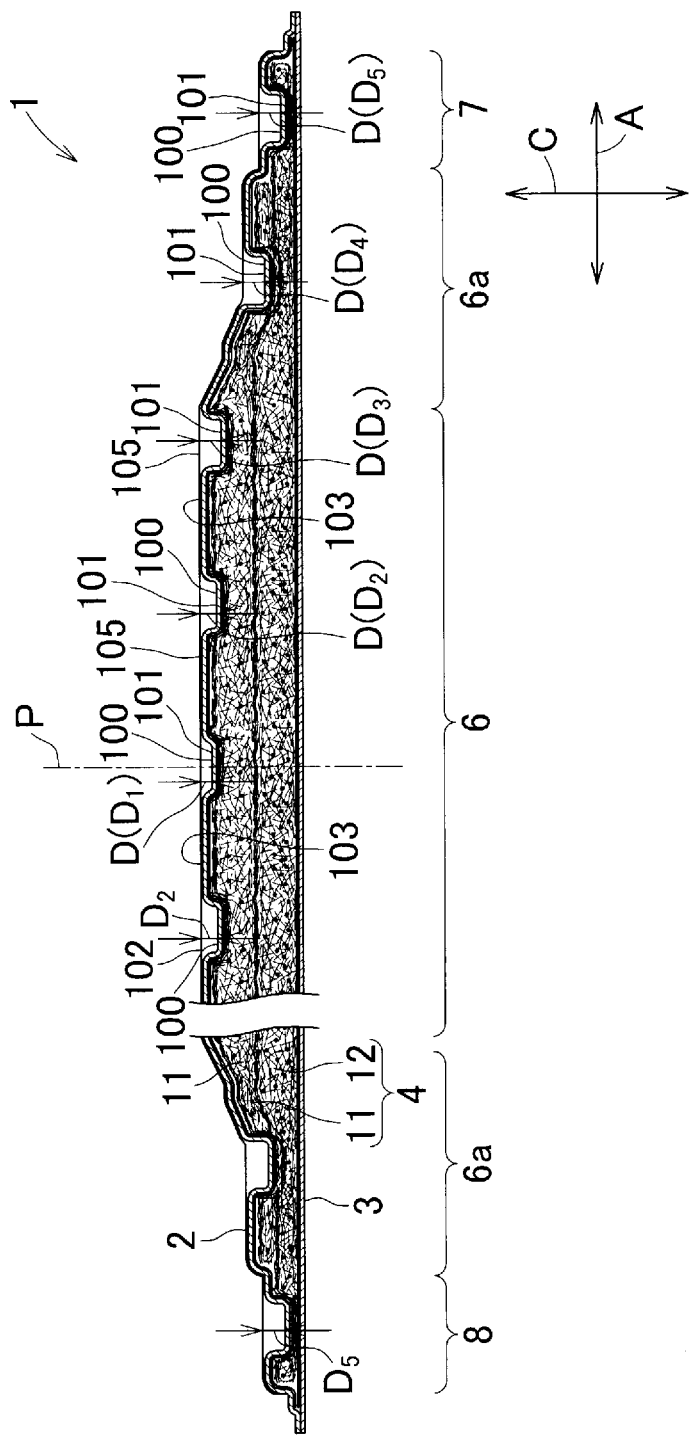
{FIG. 9}
A sectional view taken along line IX-IX in FIG. 8.

Referring to FIG. 9, in each of the compressed regions 100, the liquid-absorbent fibers 21 (See FIG. 2) contained in the upper and lower absorbent components 11, 12 are accumulated at a relatively high density and, in the non-compressed region 102, the liquid-absorbent fibers 21 are accumulated at a relatively low density. It should be noted here that, in the intermediate regions 103 in the non-compressed region 102 each defined between each pair of the adjacent compressed regions 100, the liquid-absorbent fibers 21 are accumulated at a higher density than that in the non-compressed region 102 other than the intermediate regions 103. This is because these intermediate regions 103 are more or less influenced by formation of the compressed regions 100. In other words, with regard to the state of accumulation of the liquid-absorbent fibers 21, there are formed high density accumulation regions in the compressed regions 100, middle density accumulation regions in the intermediate regions 103 and low density accumulation regions in the non-compressed region 102 other than the intermediate regions 103. Of the non-compressed region 102, a region adjacent to the side of the four sides contouring the bottom surface 101 of the compressed region 100 is also influenced by formation of the compressed region 100. In the description given hereunder, it should be appreciated that such region is not included in the term "the non-compressed region 102".

In FIG. 9, the bottom surface 101 of the compressed region 100 lies at a lower level than a surface level 105 of the non-compressed region 102 exclusive of the intermediate region 103 by the dimension D. In other words, the distance between the bottom surface 101 and the backsheet 3 is smaller than the distance between the surface level 105 and the backsheet 3. The dimension D substantially corresponds to the depth of compression worked on the pad 1. The dimension D in the pad 1 may be varied to vary the density of the compressed regions 100 in which the liquid-absorbent fibers 21 are accumulated. The term "density of the compressed region" used herein means the density of the absorbent structure 4 included by the compressed region.

Concerning the super-absorbent polymer particles 22 (See FIG. 2), it depends on the situation whether the super-absorbent polymer particles 22 are contained or not.

In FIG. 9, suffixes 1 through 5 are attached the dimensions D of the respective compressed regions 100 arranged from the transverse center line P-P toward the end region 7. Of these dimensions $D_1$ through $D_5$, the dimension $D_1$, the dimension $D_2$ and the dimension $D_3$ are gradually enlarged in this order and the dimensions $D_3$ through $D_5$ are equal one to another. The compressed regions 100 having the dimensions $D_1$ through $D_3$ are formed in the central region 6 in which the non-compressed region 102 is relatively thick and substantially uniform. The compressed region 100 having the dimension $D_4$ is formed in the intermediate region 6a extending between the central region 6 and the end region 7 or 8 and being relatively thin. The compressed region 100 having the dimension $D_5$ is formed in the end region 7 or 8 which is thinner than the intermediate region 6a. In the pad 1 having the dimension in the longitudinal direction A and the thickness varying in this manner, the density of the compressed regions 100 containing the accumulated liquid-absorbent fibers 21 exhibits the density gradient according to which the density of the compressed regions 100 gradually increases from the transverse center line P-P to the end region 7. In the pad 1, also formed is the density gradient according to which the density of the compressed regions 100 gradually increases from the transverse center line P-P to the end region 8.

FIG. 9 exemplarily shows the density gradient exhibited by the compressed regions 100 respectively having the dimensions $D_1$ through $D_3$ and a substantially uniform thickness and the density gradient exhibited by the compressed regions 100 having the dimensions $D_3$ through $D_5$ and gradually reduced thickness. With either density gradient, bodily fluid disperses toward the compressed regions 100 having a relatively high density.

With such pad 1, bodily fluid such as urine discharged, for example, onto a region in which the transverse center line P-P intersects with the longitudinal center line Q-Q quickly disperses from the transverse center line P-P toward the end region 7 and/or the end region 8 according to the density gradients defined among the compressed regions 100 and is absorbed and contained by the end regions 7, 8 and the other regions. In this pad 1, the compressed regions 100 function as the means adapted for dispersion of bodily fluid whether the dispersing surfaces 11a, 12a are present or not in the absorbent structure 4 and the end regions 7, 8 and the other regions of the pad 1 can be utilized for absorption and containment of bodily fluid.

In the pad 1 exemplarily shown in FIGS. 8 and 9, it is possible to vary the dimension a of the compressed regions 100 so that, the closer to the end region 7 and/or the end region 8, the larger the dimension a is. With the pad 1 constructed in this manner, the closer to the end region 7 and/or the end region 8, the longer the bottom surface of the compressed region 100 in the longitudinal direction A. Consequentially, bodily fluid can smoothly disperse from the central region as viewed in the longitudinal direction A toward the end region 7 and/or the end region 8.

In the pad 1 exemplarily shown in FIGS. 8 and 9, with the dimension a being kept constant, the dimension b can be varied so that, closer to the end region 7 and/or the end region 8, larger the dimension b is. With the pad 1 constructed in this manner, closer to the end region 7 and/or the end region 8, the bottom surface 101 of the compressed regions 100 is wider and the area of the bottom surface 101 is larger. In consequence, bodily fluid discharged onto the central region as viewed in the longitudinal direction A can smoothly disperse in the longitudinal direction A as well as in the transverse direction B.

It is also possible in the pad 1 to vary the dimension a and the dimension b so that, the closer to the end region 7 and/or the end region 8, the larger the dimensions a and b are. The dimension c is preferably small so far as the dimension c does not interfere with formation of the compressed regions 100.

Figure 10:
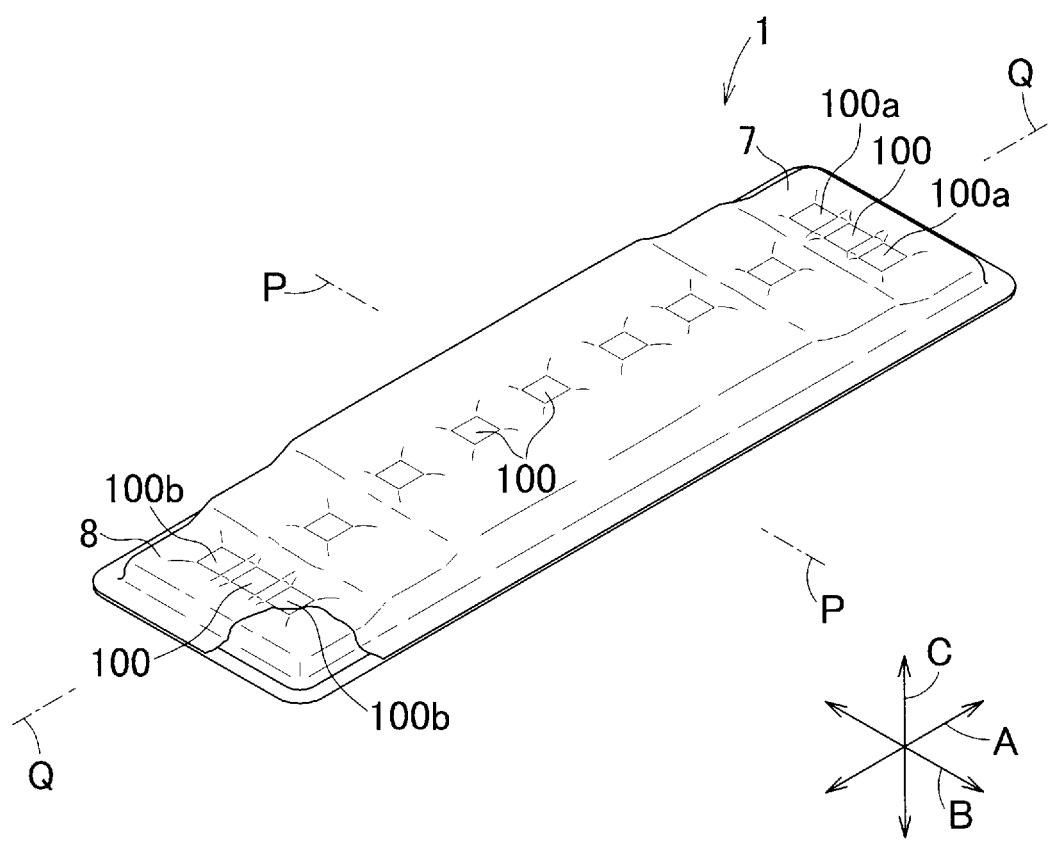
{FIG. 10}
A view similar to FIG. 8, showing further another embodiment of the present invention.

Referring to FIG. 10, it is a view similar to FIG. 8, showing further another embodiment of the present invention. However, the pad 1 shown in FIG. 10 is different from pad 1 shown in FIG. 8 in that, in addition to that the compressed regions 100 are aligned intermittently along the longitudinal center line Q-Q, additional compressed regions 100a are aligned in the transverse direction B in the end regions 7, and/or additional compressed regions 100b are aligned in the transverse direction B in the end regions 8. The additional compressed regions 100a are formed in the same manner as the compressed region 100 in the end region 7 and the additional compressed regions 100b are formed in the same manner as the compressed region 100 in the end region 8. By forming these additional compressed regions 100a, 100b as exemplarily illustrated, dispersion of bodily fluid over the end regions 7, 8 in the transverse direction B is facilitated and the end regions 7, 8 can be utilized over a wide range for absorption and containment of bodily fluid.

Figure 11:
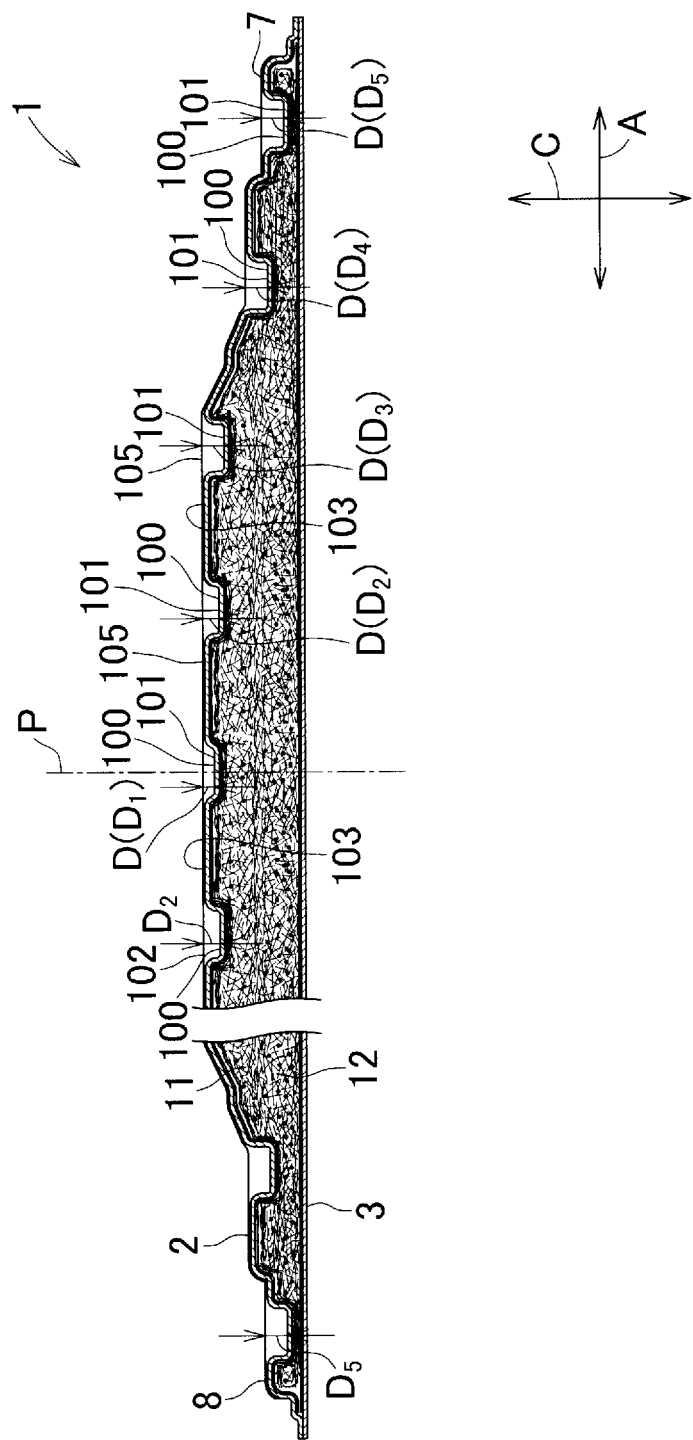
{FIG. 11}
A view similar to FIG. 9, showing an alternative embodiment of the present invention.

Referring to FIG. 11, it is a view similar to FIG. 9, showing an alternative embodiment of the present invention. The absorbent structure 4 of the pad 1 shown in FIG. 11 does not include the upper absorbent component 11 and the lower absorbent component 12 layered one on another as exemplarily shown in FIG. 3. Specifically, the absorbent structure 4 according to the present embodiment includes amass or an aggregation of absorbent materials having the same composition as the upper absorbent component 11 or the lower absorbent component 12 but not having the laminar structure and wrapped with the wrapping sheet 13 exemplarily shown in FIG. 3. Also in the pad 1 having such absorbent structure 4, the compressed regions 100 exemplarily illustrated in FIGS. 8 through 10 may be formed to obtain the bodily fluid absorbent article according to the present invention.

While the pad 1 is shown in FIGS. 1 through 11 to be rectangular, the shape of the pad 1 may be appropriately selected depending on the intended purpose. The shapes of the compressed regions 81, 100 are not limited to the rectangle and square but may be appropriately selected. It is possible to form the compressed region 100 by compressing the pad 1 from the side of the backsheet 3 toward the side of the topsheet 2 instead of compressing the pad 1 from the side of the topsheet 2 toward the backsheet 3. It is also possible in the pad 1 of FIG. 6 to replace the rows of the compressed regions 81 in the pad 1 of FIG. 6 by the compressed regions 100 exemplarily shown in FIGS. 8 and 9 and thereby to obtain the bodily fluid absorbent article according to the present invention.

Any of the arrangements of compressed regions, as discussed with respect to FIGS. 6 and 8 to 11 may be provided in the embodiments of FIGS. 1 to 4. Moreover, the absorbent structures, as discussed with respect to FIGS. 3, 4 and 7 may be swapped with one another. Various further embodiments will be realized by those skilled in the art by the combination of various features from the different embodiments within the scope of the claims.

The first, second and third aspects of the present invention described above may be arranged in at least the following features:

There is provided a bodily fluid absorbent article having a longitudinal direction and a thickness direction and comprising a liquid-pervious topsheet, a liquid-pervious or liquid-impervious backsheet and an absorbent structure sandwiched between the top- and backsheets in this order as viewed in the thickness direction. The absorbent structure includes a mass or an aggregation of liquid-absorbent materials at least including liquid-absorbent fibers, and wrapped with a wrapping sheet and a dispersing surface facilitating bodily fluid to be dispersed, and wherein at least a portion of the wrapping sheet located above as viewed in the thickness direction is liquid-pervious.

The first aspect further includes the absorbent structure including an upper absorbent component and a lower absorbent component both lying inside the one or more wrapping sheets and layered one on another in the thickness direction and the dispersing surface includes a surface of the upper absorbent component which is kept in contact with the lower absorbent component or a surface of the lower absorbent component which is kept in contact with the upper absorbent component; and the liquid-absorbent fibers in the dispersing surface extend along the dispersing surface. Preferably, the orientation of the liquid-absorbent fibers in the longitudinal direction or the transverse direction, respectively, is higher in the dispersing surface than in a region of the respective absorbent component contacting the dispersing surface.

The first aspect may include at least the following embodiments.

(i) Both the upper absorbent component and the lower absorbent components may include dispersing surfaces, wherein the dispersing surface of the upper absorbent component is kept in contact with the wrapping sheet and the dispersing surface of the lower absorbent component is kept in contact with the upper absorbent component.

Alternatively, both the upper absorbent component and the lower absorbent components may include dispersing surfaces, wherein the dispersing surface of the upper absorbent component is kept in contact with the lower absorbent component and the dispersing surface of the lower absorbent component is kept in contact with the wrapping sheet.

(ii) Either or both absorbent components that are provided with the dispersing surface, wherein the dispersing surface is unitarily formed with the absorbent layer.

(iii) The dispersing surface preferably extends over the entire surface of the absorbent layer.

(iv) The orientation of the liquid-absorbent fibers in the dispersing surface is preferably greater than the orientation of the liquid-absorbent fibers in the absorbent layer.

(v) The orientation of the liquid-absorbent fibers in the absorbent layer preferably decreases as the distance from the dispersing surface in the thickness direction of the absorbent component increases.

(vi) The liquid-absorbent fibers are oriented in the one of the dispersing surface so as to extend in at least one of the longitudinal direction and the transverse direction and thereby the dispersion velocity is improved.

(vii) The density of the liquid-absorbent fibers in the absorbent layer preferably decreases as the distance from the dispersing surface in the thickness direction of the absorbent component increases.

(viii) The upper absorbent component and the lower absorbent component may contain super-absorbent polymer particles and a content percentage by mass of the super-absorbent polymer particles in the upper absorbent component may be lower than that in the lower absorbent component.

(ix) The dispersing surfaces may contain none of the super-absorbent polymer particles.

(x) The upper and lower absorbent components may be the same size in the length and/or width dimensions. Alternatively, either the upper or lower absorbent component may be longer and/or wider than the other of the upper and lower components.

(xi) The topsheet and the wrapping sheet, the wrapping sheet and the upper absorbent component, the lower absorbent component and the wrapping sheet, and the second wrapping sheet and the backsheet may be bonded to one another.

(xii) Both the upper absorbent component and the lower absorbent component may include central sections as viewed in one of the longitudinal direction and the transverse direction, which are dimensioned to be thicker than respective end sections extending outside the central sections as viewed in one of the respective longitudinal and transverse directions.

(xiii) The central sections of the upper and lower absorbent components may be the same size in the length and/or width dimensions. Alternatively, either the central section of the upper absorbent component or the central section of the lower absorbent component may be longer and/or wider than the central section of the other of the upper and lower absorbent components.

(xiv) The central sections of the upper absorbent component and the lower absorbent component may respectively define regions each containing the liquid-absorbent fiber in a range of 300 to 400 g/m² by mass and the end sections respectively define regions each containing the liquid-absorbent fiber in a range of 100 to 250 g/m² by mass.

(xv) The upper absorbent component and the lower absorbent component may respectively contain the super-absorbent polymer particles in a range of 35 to 75% by mass per unit area. A plurality of compressed regions may be formed by locally compressing the upper and/or lower absorbent component in the thickness direction, wherein the plurality of compressed regions are arranged intermittently in the longitudinal direction of the absorbent article.

(xvi) The compressed regions may have respective areas gradually enlarging from a central region of the bodily fluid absorbent article toward opposite end regions in the longitudinal direction.

(xvii) The compressed regions may have respective densities gradually increasing from a central region of the bodily fluid absorbent article toward opposite end regions in the longitudinal direction.

The second aspect further includes the following features:

The dispersing surface includes a plurality of compressed regions formed by locally compressing the absorbent structure in the thickness direction, the compressed regions being arranged intermittently in the longitudinal direction, and the compressed regions having respective areas gradually enlarging from a central region of the bodily fluid absorbent article toward opposite end regions in the longitudinal direction.

The second aspect may include an absorbent structure in accordance with the first aspect and any of the embodiments thereof, as defined in the preceding paragraphs. The second aspect may further include at least the following embodiments.

(i) A plurality of the compressed regions may be formed in a middle region of the absorbent structure as viewed in the transverse direction. The compressed regions may extend along the longitudinal centerline of the absorbent article.

(ii) A plurality of the compressed regions may be formed on both sides of the absorbent structure as viewed in the transverse direction. The compressed regions may extend along each of the transversely spaced side edges of the absorbent structure.

(iii) The absorbent structure may additionally include in the end regions on both sides of the compressed regions formed in the middle in the transverse direction, with second compressed regions by locally compressing the absorbent structure in the thickness direction.

(iv) The absorbent structure may be formed so that its thickness is gradually reduced from the middle region in the longitudinal direction toward the end regions and the respective densities of the compressed regions arranged in the longitudinal direction gradually increase from the central region in the longitudinal direction toward the end regions.

(v) The absorbent structure may include an upper absorbent component and a lower absorbent component both lying inside the one or more wrapping sheets and stacked one on another in the thickness direction and the compressed regions are formed by compressing the absorbent structure from one of the upper absorbent component and the lower absorbent component toward the other.

The third aspect further includes the dispersing surface including a plurality of compressed regions formed by locally compressing the absorbent component in the thickness direction so as to be arranged intermittently in the longitudinal direction so that the compressed regions having respective densities gradually increasing from a central region of the bodily fluid absorbent article toward opposite end regions in the longitudinal direction.

The third aspect may include an absorbent structure in accordance with the first aspect and any of the embodiments thereof, as defined in the preceding paragraphs. The third aspect may further include at least the following embodiments.

(i) The depth of the compressed regions in the thickness direction may gradually increase from a central region of the bodily fluid absorbent article toward opposite end regions in the longitudinal direction.

(ii) A plurality of the compressed regions may be formed in a middle region of the absorbent structure as viewed in the transverse direction. All or some of the compressed regions may extend along the longitudinal centerline of the absorbent article.

(iii) The size of the compressed regions may remain constant. Alternatively, the compressed regions may have respective areas gradually enlarging from a central region of the bodily fluid absorbent article toward opposite end regions in the longitudinal direction.

(iv) The spacing between the compressed regions may remain constant.

(v) The compressed regions are preferably square.

The first, second and third aspects may include the following embodiment.

The liquid-absorbent fibers may be composed of at least one of fluff wood pulp and fluff wood pulp combined with different liquid-absorbent fibers.

REFERENCE SIGNS LIST 1 bodily fluid absorbent article (urine absorbent pad)
2 topsheet
3 backsheet
4 absorbent structure
7 region (end region)
8 region (end region)
11 upper absorbent component
11a dispersing surface (upper dispersing surface)
11c dispersing surface (lower dispersing surface)
12 lower absorbent component
12a dispersing surface (lower dispersing surface)
12c dispersing surface (lower dispersing surface)
13 wrapping sheets
13a, 13b wrapping sheets (first and second wrapping sheets)
21 liquid-absorbent fibers
22 super-absorbent polymer particles
31 central region (first upper section)
32 end region (second upper section)
33 end region (third upper section)
41 central region (first lower section)
42 end region (second lower section)
43 end region (third lower section)
100 compressed region
100a second compressed region
100b second compressed region
A longitudinal direction
B transverse direction
C thickness direction

The invention claimed is:

1. A bodily fluid absorbent article having a longitudinal direction and a thickness direction and comprising:
    a liquid-pervious topsheet;
    a liquid-pervious or liquid-impervious backsheet; and an absorbent structure sandwiched between the top- and backsheets as viewed in the thickness direction, wherein the absorbent structure comprises a mass or an aggregation of liquid-absorbent materials, at least including liquid-absorbent fibers, wrapped with one or more wrapping sheets, and dispersing surface facilitating bodily fluid to be dispersed, and wherein at least a portion of one of the wrapping sheets located above the absorbent structure as viewed in the thickness direction is liquid-pervious, wherein:

the absorbent structure further comprises an upper absorbent component and a lower absorbent component each comprising a mass or an aggregation of liquid-absorbent materials including at least liquid-absorbent fibers and each lying inside the one or more wrapping sheets and layered one on another in the thickness direction;

a dispersing surface comprising a surface of the upper absorbent component which is kept in contact with the lower absorbent component or a surface of the lower absorbent component which is kept in contact with the upper absorbent component; and the liquid-absorbent fibers in the dispersing surface extend along the dispersing surface, wherein both the upper absorbent component and the lower absorbent component include central sections as viewed in one of the longitudinal direction and the transverse direction, which are dimensioned to be thicker than respective end sections extending outside the central sections as viewed in one of the respective longitudinal and transverse directions.

2. The bodily fluid absorbent article defined by claim 1, wherein the upper absorbent component and the lower absorbent component contain super-absorbent polymer particles and a content percentage by mass of the super-absorbent polymer particles in the upper absorbent component is lower than a content percentage by mass of the super-absorbent polymer particles in the lower absorbent component.

3. The bodily fluid absorbent article defined by claim 2, wherein the dispersing surfaces contains none of the super-absorbent polymer particles.

4. The bodily fluid absorbent article defined by claim 2, wherein the upper absorbent component and the lower absorbent component respectively contain the super-absorbent polymer particles in a range of 35 to 75% by mass per unit area.

5. The bodily fluid absorbent article defined by claim 1, wherein the central sections of the upper absorbent component and the lower absorbent component respectively define regions each containing the liquid-absorbent fibers in a range of 300 to 400 $g/m^2$ by mass and the end sections respectively define regions each containing the liquid-absorbent fibers in a range of 100 to 250 $g/m^2$ by mass.

* * * * *